United States Patent [19]
Kovacevic

[11] Patent Number: 5,289,826
[45] Date of Patent: Mar. 1, 1994

[54] TENSION SENSOR

[75] Inventor: Nebojsa Kovacevic, Minneapolis, Minn.

[73] Assignee: N. K. Biotechnical Engineering Co., Minneapolis, Minn.

[21] Appl. No.: 847,590

[22] Filed: Mar. 5, 1992

[51] Int. Cl.[5] .................................................. A61B 5/103
[52] U.S. Cl. ................................ 128/774; 73/862.471; 73/862.634; 606/102
[58] Field of Search .................. 128/774, 782, 721; 73/831, 832, 833, 856, 859, 862.391, 862.392, 862.451, 862.471, 862.472, 862.473, 862.474, 862.627, 862.632, 862.638, 862.639, 862.634, 379; 33/512, 787, 788, 789, 790; 338/6; 606/86, 102

[56] References Cited

U.S. PATENT DOCUMENTS

| | | | |
|---|---|---|---|
| 3,319,338 | 5/1967 | De Nicola | 33/790 |
| 3,782,365 | 1/1974 | Pinna | 128/2 R |
| 3,789,508 | 2/1974 | Meline | 33/788 |
| 3,937,212 | 2/1976 | Fletcher et al. | 128/2 S |
| 4,058,005 | 11/1977 | Barnett | 73/88.5 R |
| 4,132,224 | 1/1979 | Randolph | 128/2 S |
| 4,163,126 | 7/1979 | Van Mastrigt | 200/61.13 |
| 4,217,912 | 8/1980 | Hubmann et al. | 128/774 |
| 4,223,443 | 9/1980 | Bachmann et al. | 33/148 D |
| 4,249,417 | 2/1981 | Feldstein et al. | 73/141 |
| 4,294,015 | 10/1981 | Drown et al. | 33/788 |
| 4,313,446 | 2/1982 | Kanatani | 128/744 |
| 4,322,707 | 3/1982 | Ort | 338/2 |
| 4,491,021 | 1/1985 | Meline | 73/767 |
| 4,590,808 | 5/1986 | Lightfoot et al. | 73/862.48 |
| 4,641,661 | 2/1987 | Kalarickal et al. | 128/744 |
| 4,644,785 | 2/1987 | Doyle | 73/151 |
| 4,813,435 | 3/1989 | Arms | 128/774 |
| 4,876,900 | 10/1989 | Carney et al. | 73/862.48 |
| 4,911,004 | 3/1990 | Leon | 73/168 |
| 4,950,271 | 8/1990 | Lewis et al. | 606/102 |
| 5,027,828 | 7/1991 | Kovacevic et al. | 128/774 |
| 5,056,530 | 10/1991 | Butler et al. | 128/774 |

OTHER PUBLICATIONS

Article entitled "Miniature Force Transducer for Myocardial Stimulation and Local Tension Measurements", *IEEE Transactions of Biomedical Engineering*, vol. BME-26, No. 2 (Feb. 1979) Hasin et al.

*Primary Examiner*—Stephen C. Pellegrino
*Assistant Examiner*—Guy V. Tucker
*Attorney, Agent, or Firm*—Westman, Champlin & Kelly

[57] ABSTRACT

A force sensor is used to determine tension forces present in a portion of tissue adjacent a body joint. A support plate is inserted under a tissue portion through two spaced apart incisions. The ends of the support plate are exposed and are mounted to a sensor frame along with a flexure member. A load plate mounted to the flexure member transfers force loads sensed from the tissue portion to the flexure member. A strain gage is mounted to the flexure member to provide an output signal representative of the force on the flexure member and thus forces in the tissue.

27 Claims, 3 Drawing Sheets

5,289,826

TENSION SENSOR

BACKGROUND OF THE INVENTION

The present invention relates to a force sensor for determining forces present in a portion of tissue surrounding a body joint.

The measuring of forces in ligaments for joints is shown in the prior art, such as the device shown in U.S. Pat. No. 4,950,271. This device measures the ligament forces and then the surgeon repairing a joint adjusts the length and the positioning of the ligaments to achieve the desired forces. This patent discloses measuring the ligament loading forces, whereas the present invention applies to any tissue surrounding the joint.

Another common problem solved by the present invention is that of achieving uniform measurements of forces and comparisons to insure satisfactory operations.

SUMMARY OF THE INVENTION

The present invention relates to a force sensor disposed in an incision and engaged with tissue which carries loads which are to be measured. A portion of tissue, alongside a joint such as a knee, is incised with a slit between the tissue and bone and a support plate is slipped into the slit so the tissue is over the support plate and both ends of the support plate are exposed. The support plate is supported on a frame on the exterior of the tissue.

A load plate bears on the exterior of the tissue, and is supported back to the frame through a load sensing flexure member. Tension loads in the tissue change when the joint is moved. The tension is sensed by movement of the load plate and transferred from the load plate to the flexure member. The flexure member has multiple parallel plates essentially forming cantilevered beam assembly that deflects under forces. Strain gages are mounted on the flexure member to sense the force transferred by the load plate, and to output a signal representative of the force in the tissue.

A purpose of the present invention is to permit achieving substantial equality in forces of the tissue as the joint is moved before and after replacement of a joint with a prosthesis. The surgeon measures the tension in the tissue prior to surgery, as the natural joint is moved. The joint is then removed and replaced with a prosthesis. The tension in the tissue is again measured at a plurality of angular positions of the prosthesis joint. If the surgeon determines the appropriate tissue tension force is not present with the new prosthesis, the surgeon can perform curative steps such as additional joint resectioning or the implantation of spacers to achieve substantial equality in force readings before and after surgery.

DETAILED DESCRIPTION OF THE PREFERRED EMBODIMENTS

Figure 1:
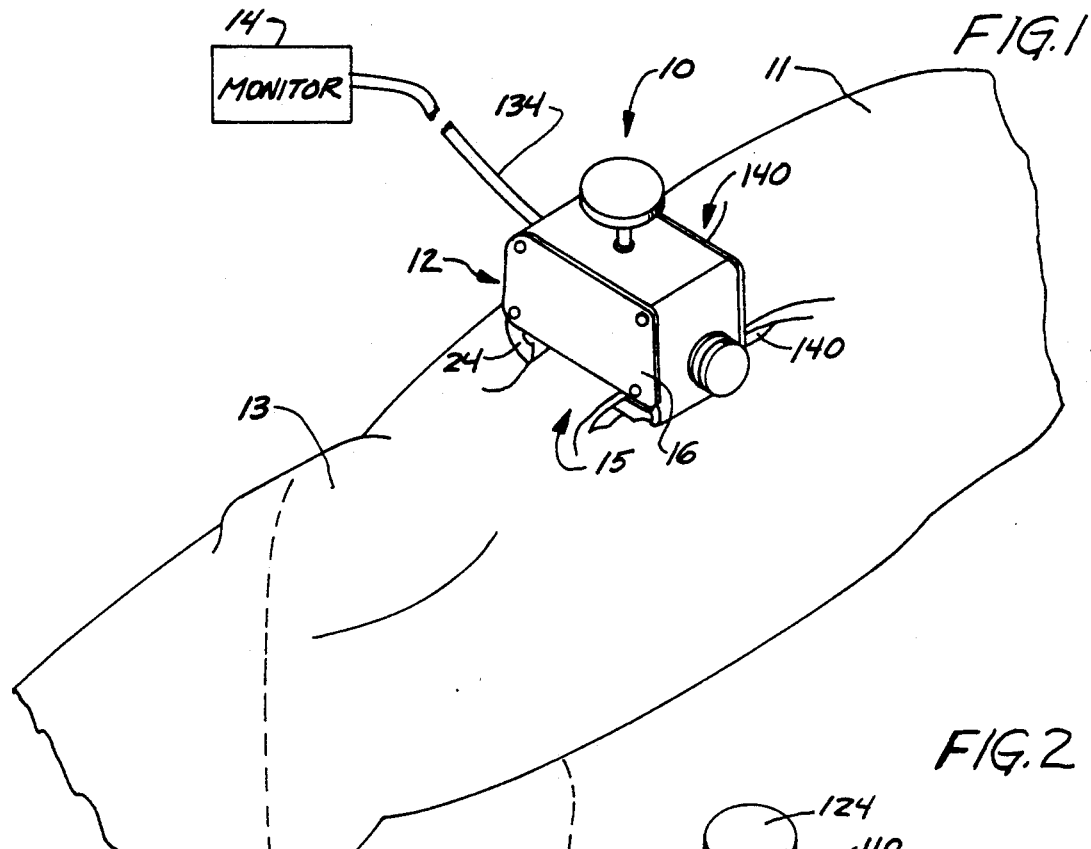
FIG. 1 is a side schematic view of a leg and knee joint with a sensor of the present invention mounted near the joint.

FIG. 1 illustrates a portion of a human leg 11 including a knee joint 13. In this view, the leg 11 is illustrated as extended with solid lines, while dashed lines illustrate the leg 11 in a bent or flexed position due to articulation of the knee joint 13. A soft tissue tension measuring system of the present invention is shown in perspective at 10. The system 10 comprises a sensor 12 that engages a portion of soft tissue adjacent to and surrounding the knee joint 13. Preferably the sensor may be placed on lateral sides of the knee. Sensor 12 is connected to a monitoring circuit indicated generally at 14. Sensor 12 is installed after making a pair of incisions or slits that are spaced apart and parallel. The layer of tissue is separated from supporting layers of bone and/or other tissue and a support plate 24 is slipped through the slits and under the layer of tissue to be measured. The sensor is clamped to the base plate and has a load plate that is adjusted until it bears on the exterior of the tissue. Loads are measured as the joint is moved. The sensor output is connected to the monitoring circuit 14. The system 10 provides a quantitative measurement of tension force loads present on the soft tissue layer 15 when the joint 13 is articulated.

Figure 2:
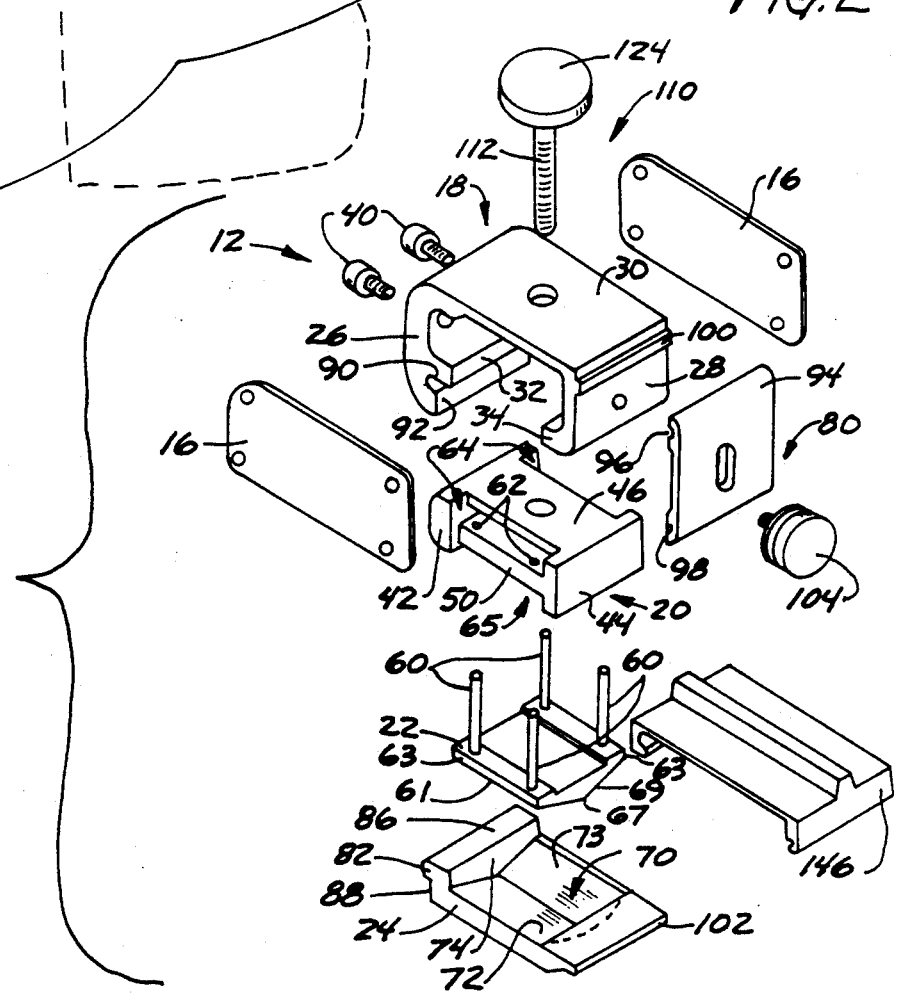
FIG. 2 is an exploded perspective view of the sensor.
Figure 3:
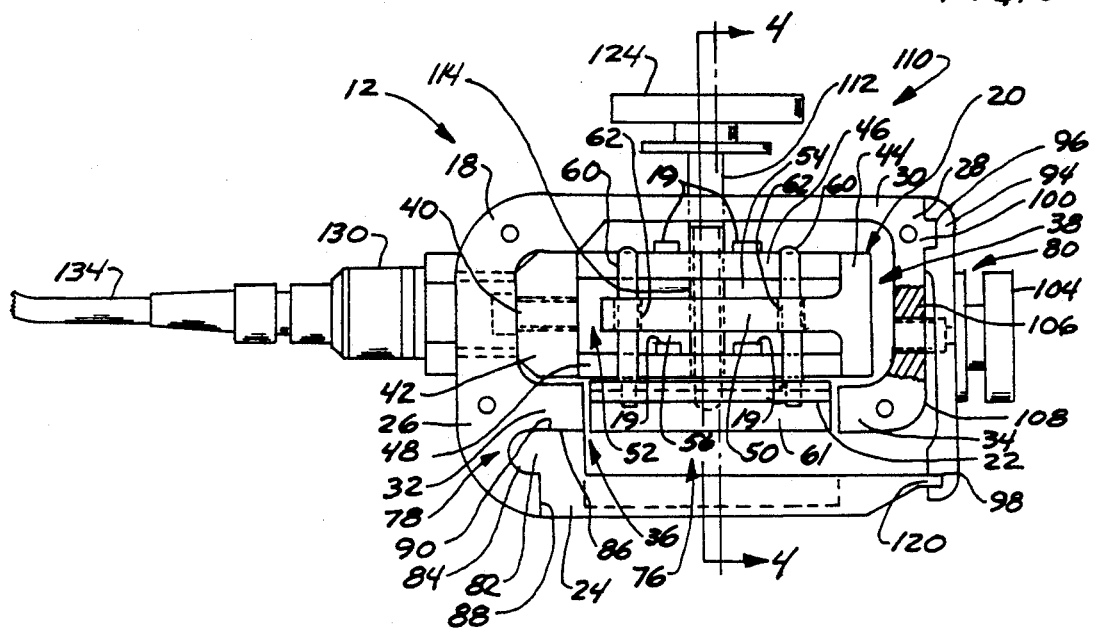
FIG. 3 is a side view of the sensor with the side plates removed.

Referring to FIGS. 2 and 3, sensor 12 is illustrated with components thereof in exploded relationship (FIG. 2), and with a side cover 16 removed in a side elevational view (FIG. 3). The sensor 12 includes a frame 18, which supports a flexure or load measuring member 20. Load plate 22 is slidably mounted relative to the flexure member 20. The support plate 24 is removably mounted on the frame 18 so the support plate 24 can be slipped under the tissue to be sensed and the frame 18 installed on the exposed ends of the support plate 24. Frame 18 comprises an integral, U-shaped, inverted channel having side walls 26 and 28, and an upper wall 30. Inwardly extending flanges 32 and 34 (see FIG. 3) are integrally formed on the lower ends of side walls 26 and 28, respectively, and define a slot or opening 36. A channel or cavity 38 is defined above slot 36 by inwardly facing surfaces of walls 26, 28 and 30, and by the upper surfaces of flanges 32 and 34.

Flexure member 20 is located within channel 38 above slot 36. Flexure member 20 is secured to the frame 18 at one end only, at an inner surface of wall 26 with conventional means such as threaded bolts 40. In the embodiment as shown, flexure member 20 is a cantilevered member using an integral, parallel plate assembly that responds to forces by deflecting. Flexure member 20 includes opposed end connector walls 42 and 44 that are spaced apart and integrally attached to an upper beam or plate 46 and to a lower beam or plate 48. A third load sensing beam 50 is integrally attached to, and cantilevered from, wall 44 to extend inwardly therefrom toward the inner surface of wall 42 generally parallel to beams or plates 46 and 48. A slot or gap 52 separates the inwardly extending end of beam 50 from the inner surface of wall 42, while slots 54 and 56 provide a space or gap between opposed surfaces of plate 50 with respect to plates 46 and 48, respectively. Flexure member 20 thereby forms a cantilevered beam assembly wherein the center beam 50 is attached to connector wall 44, while the beams or plates 46 and 48 join the wall 44 to the wall 42, and wherein the flexure member 20 is attached to frame 18 only at wall 26 through end wall 42, with bolts 40.

Figure 4:
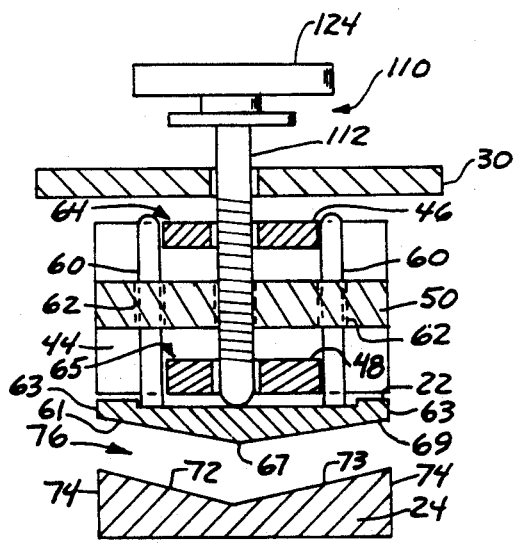
FIG. 4 is a vertical sectional view taken on the line 4—4 in FIG. 3.

Forces to be measured are applied to flexure member 20 through load plate 22. Load plate 22 is oriented and guided with respect to slot 36 through plate 50 through upward extending guide posts 60. The guide posts 60 align with and slide within corresponding apertures 62 in plate 50 to form a low-friction, stable, slidable connection and to align the load plate 22 relative to the support plate 24 and flexure member 20. As shown in FIGS. 2 and 4, guide posts 60 do not en either upper or lower plate 46 or 48, but rather are spaced from side edges of plate 46 in recesses 64. Similar lower clearance recesses 65, are formed in lower plate 48. As with upper recesses 64 adjacent upper plate 46, guide posts 60 extend through the lower clearance recesses 65 without contacting the side edges of lower plate 48.

Load plate 22 and support plate 24 together are used to engage and encompass the portion or layer of soft tissue 15. The support plate 24 is slipped in under layer 15 after the incisions are made. The frame 18 then clamps the support plate in place, as will be explained. The support plate 24 is below the tissue layer and the load plate is on the exterior. Referring to FIG. 2 and FIG. 4, load plate 22 has inclined lower surfaces 61, 69 that extend downwardly from side edges 63 to meet along a common center line 67 to form a generally wedge shaped lower surface. Support plate 24 includes a depression 70 formed by a concave upper surface thereof declining surface upper portions 72, 73. Surface portions 72, 73 extend downwardly and inwardly from opposed side edges 74 of support plate 24 to generally correspond to the opposed outer surfaces 61, 69 of load plate 22.

Support plate 24 is removably attached to frame below the load plate 22 with a tongue and groove connection joint 78 at one end of support plate 24 and a clamp assembly 80 at the other end. As shown, joint 78 comprises a rib 82 extending outwardly, and along an end surface of support plate 24. A corresponding groove 84 in a lower portion of side wall 26 receives rib 82. When support plate 24 is positioned as shown in FIG. 3, surfaces 86 and 88 of support plate 24 contact opposed surfaces 90 and 92 of flange 32 and the lower portion of side wall 26, respectively, to prevent substantial angular displacement or other shifting of support plate 24.

Clamp assembly 80 secures the opposite end of support plate 24 to frame 18. Clamp assembly 80 includes a removable clamp plate 94 having inwardly facing upper and lower grooves 96 and 98. Upper groove 96 engages an outwardly extending flange 100 on side wall 28, while lower groove 98 engages an outside edge lip 102 of support plate 24. A removable clamp screw 104 threaded into a threaded aperture 106 in side wall 28 secures clamp plate 94 to wall 28 which in turn secures support plate 24 with respect to frame 18. A gap 108 is provided between the outer surface of wall 28 and the inner surface of clamp plate 94 to insure that the clamp plate tightly clamps the support plate 24, when the clamp screw 104 is tightened.

As stated above, load plate 22 and support plate 24 together are used to engage soft tissue layer or portion 15 to measure tension forces therein. These tension forces are measured by locating soft tissue portion 15 in gap 76 between load plate 22 and support plate 24. With clamp assembly 80 properly affixed to frame 18 to secure placement of support plate 24, load plate 22 is displaced downwardly to engage soft tissue portion 15 with an adjustable press assembly 110. In the embodiment shown, press assembly 110 includes a threaded bolt 112 that engages a threaded aperture 114 in plate or beam 50. Bolt 112 slightly extends through top plate 46 and lower plate 48 of the flexure assembly, and a lower end of the bolt 112 contacts an upper surface of load plate 22. Bolt 112 extends upwardly through wall 30 as well. A head 124 is attached to an upper end of bolt 112 for manual rotation.

As constructed, rotation of head 124, and thus bolt 112, causes selective displacement of the lower bolt end with respect to plate 50 thereby in turn displacing load plate 22 with respect to support plate 24. With tissue layer or portion 15 located in gap 76 between load plate 22 and support plate 24, rotation of bolt 112 causes the soft tissue portion 15 to be clamped or "sandwiched" between load plate 22 and support plate 24. The clamping force is developed through bending stress in plate 50 and the flexure member 20 as a whole. Strain gages 19, such as semiconductor or piezo-electric sensors formed within or located on surfaces of the flexure member 20, respond to the deflection thereof, providing an output signal, typically an electric signal, that corresponds or represents the tension forces in the soft tissue portion 15. Leads for the sensor used are connected to a suitable wiring connector 130 that is conventionally mounted on frame 18. A cable 134 also connected to connector 130 provides the output signal to the monitoring circuit 14. Monitoring circuit 14 amplifies, conditions, and transforms the output signal for display and/or recording in appropriate tension units. With articulation of the joint, the tension within the soft tissue portion 15 can be monitored at varied positions of articulation.

The soft tissue tension measuring system 10 described above is particularly useful during implantation of a prosthetic joint for a corresponding natural joint, such as the knee joint 13 shown in FIG. 1. Referring to FIG. 1, as mentioned, two longitudinal incisions 140 are made in the soft tissue near the joint 13 generally parallel to tension forces developed in the soft tissue with articulation of the joint 13. The incisions 140 are appropriately spaced such that the soft tissue layer or portion 15 extending therebetween has lateral dimensions less than or equal to the length of depression 72 in support plate 24. Although the soft tissue portion 15 may be selected from any portion of the soft tissue that responds in tension to articulation of the joint 13, when measuring soft tissue tension around a knee joint the incisions 140 are preferably made along the side of the joint 13 as generally indicated by dashed lines 141.

The clamp plate 94 is removed from frame or base portion 18 thereby detaching support plate 24. The layer or portion 15 of soft tissue is lifted from supporting layers and bone, and support plate 24 is positioned below the soft tissue portion 15 with opposite ends extending out through the incisions 140. Frame 18 is then reconnected to support plate 24 through connection joint 78, and clamp plate 94.

With the sensor 12 properly positioned and the leg 11 extended so that the joint 13 is unarticulated, bolt 112 is rotated to displace load plate 22 toward support plate 24 to clamp the soft tissue portion 15 therebetween at a desired force level. An initial soft tissue tension force reading is then obtained from monitoring circuit 14. The joint 13 is then articulated to develop tension forces in the soft tissue portion 15. The tension changes at different positions of the joint. Corresponding soft tissue tension force measurements are recorded. In the preferred embodiment, the joint is articulated a number of times to provide a plurality of measurements for each of a plurality of angular positions. For each position, the average soft tissue force tension is calculated and recorded. The frame 18 can then be removed from the support plate 24 and a cover plate 146, shown in FIG. 5, of plastic or other material is clamped on the support plate 24 so it can remain in place during subsequent surgery.

Using conventional surgery, a surgeon then replaces the knee joint with a suitable prosthesis. The knee joint is again articulated, after the frame 18 and sensor is placed onto the support plate 24. The soft tissue tension forces are measured by sensor 12 as the prosthesis is articulated. If average soft tissue force tension data is being measured, the joint is articulated a suitable number of times to obtain sufficient data at each position to calculate an average value.

The surgeon then analyzes the soft tissue tension force data obtained with the prosthesis in place to determine if appropriate tension forces are present for the full range of articulation. Having previously measured the soft tissue tension forces with the original, natural, and now removed joint in place, the surgeon's analysis will commonly include comparing the soft tissue tension force data obtained with the prosthesis in place with the data associated with the removed joint. If the surgeon determines that appropriate soft tissue tension is not present with the new prosthesis, for example if there exists substantially unequal soft tissue tension forces between the prosthesis and the removed joint, the surgeon can perform curative steps such as additional joint resectioning or the implantation of spacers to achieve substantial equality between force readings.

Figure 7:
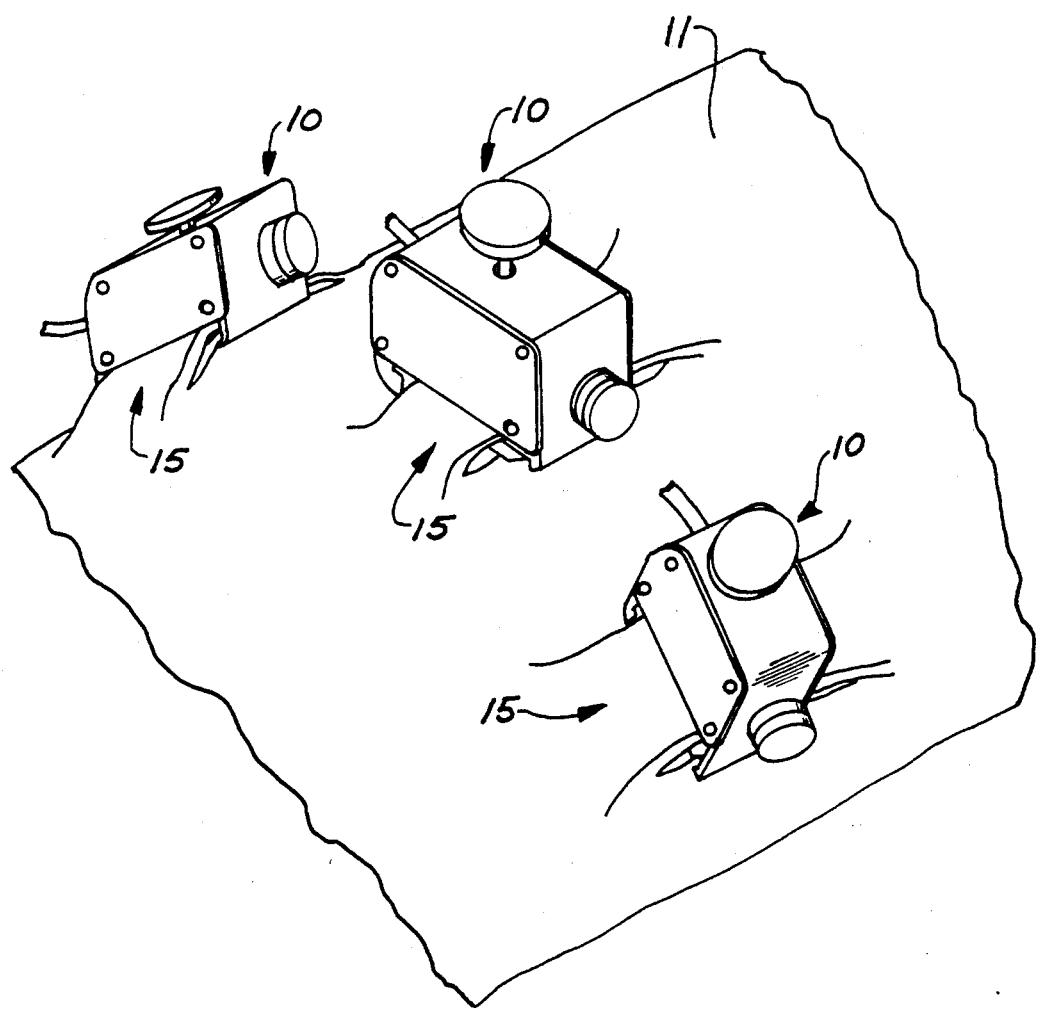
FIG. 7 is a perspective view of a leg with multiple sensors mounted on the leg.

In the preferred embodiment, proper soft tissue force tension measuring may entail soft tissue measurements taken at a plurality of locations located around the joint. As illustrated in FIG. 7, a plurality of support plates 24 can be located under several different soft tissue portions surrounding the joint. Multiple sensors can be used as shown in FIG. 7, or a single sensor 12 can be selectively mounted to each of a plurality of support plates, installed as discussed above, to monitor forces present in each of the selected soft tissue portions before and after prosthesis implantation. By recording the initial soft tissue force tension measurement at each location before removing the natural joint, and recording the soft tissue force tension measurement at each location after the joint has been removed and replaced with a prosthetic joint, the soft tissue force tension data set obtained prior to joint removal can be accurately compared to the corresponding soft tissue force tension data set obtained after joint removal.

Figure 5:
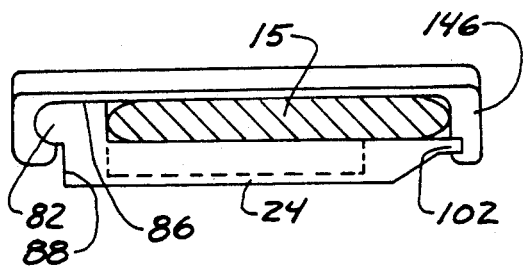
FIG. 5 is a side view of the support plate and a temporary cover plate.
Figure 6:
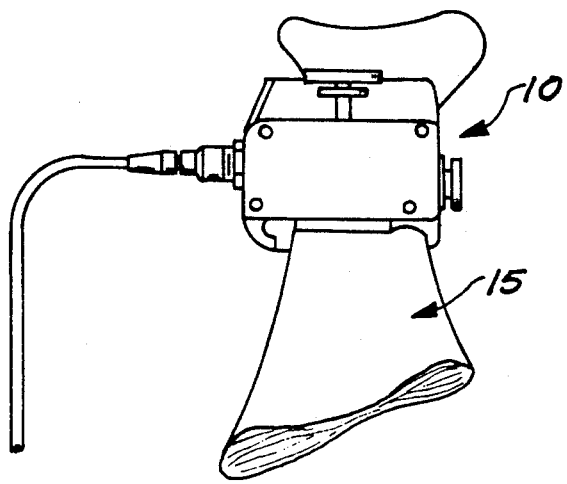
FIG. 6 is a view showing a section of tissue held in the sensor.

As seen in FIG. 5, the temporary cover plate 146, used to retain support plates, is made from a flexible material such as plastic and has corresponding grooves similar to groove 98 in clamp plate 94 and groove 84 in wall 26 is shown. A cover plate 146 may be attached to each support plate 24 not currently connected to a frame 18. Cover plate 146 maintains the position of the corresponding support plate during surgery and articulation of the joint while other selected soft tissue portions are being measured.

Although the present invention has been described with reference to preferred embodiments, workers skilled in the art will recognize that changes may be made in form and detail without departing from the spirit and scope of the invention.

What is claimed is:

1. An apparatus to measure forces in a portion of tissue comprising:

a frame;

a flexure member cantilevered from the frame, the flexure member comprising parallel flexure plates and a connector wall, the flexure plates having first ends thereof attached to the frame and second ends thereof joined with the connector wall;

a load plate mounted to the flexure member;

support means mounted to said frame and opposite said load plate for supporting a tissue portion to be measured;

means for adjusting the load plate to clamp the tissue portion between said load plate and said support means; and sensing means connected to said flexure member for providing an output signal representative of flexure forces on said flexure member, said flexure member being responsive to loading exerted between the load plate and the support means.

2. The apparatus as in claim 1 wherein said load plate includes guide means to align the load plate relative to the support means and flexure member, the guide means being slidably operative with the flexure member.

3. The apparatus as in claim 2 wherein said guide means comprises a guide post connected to the load plate.

4. The apparatus as in claim 1 wherein said load plate has a lower surface which is wedge shaped in cross section.

5. The apparatus as in claim 4 wherein said support means has a wedge shaped depression corresponding to the wedge shaped surface of the load plate.

6. The apparatus as in claim 1 wherein said support means is removably mounted to the frame.

7. The apparatus as in claim 1 wherein said means for adjusting the load plate comprises an adjustment mechanism joined to the flexure member, the adjustment mechanism adjusting the relative spacing between the load plate and the flexure member.

8. The apparatus as in claim 7 wherein said adjustment mechanism comprises a threaded rod mating with a threaded aperture in the flexure member.

9. The apparatus as in claim 8 and further comprising a beam joined to said flexure member, said beam having said threaded aperture.

10. The apparatus as in claim 9 wherein said beam is joined to said connector wall.

11. The apparatus as in claim 9 wherein said beam is disposed between said parallel plates.

12. The apparatus as in claim 9 and further comprising a guide post connected to the load plate, and wherein said beam includes a guide aperture, said guide post being slidable within said guide aperture to align said load plate with said support means.

13. The apparatus as in claim 9 and further comprising a plurality of guide posts connected to the load plate, and wherein said beam includes a plurality of guide apertures, each said guide post being slidable within one of the guide apertures to align said load plate with said support means.

14. A force sensor for determining tension forces present in a portion of tissue surrounding a body joint, the force sensor comprising:

a frame;

a flexure member cantilevered from the frame, the flexure member comprising parallel flexure plates and a connector wall, the flexure plates having first ends thereof attached to the frame and second ends thereof joined with the connector wall;

a load plate mounted to the flexure member;

support means mounted to said frame and opposite said load plate for supporting a portion of tissue to be measured;

sensing means mounted to the flexure member for sensing tension forces, the tension forces being transferred from the load plate to the flexure member;

a press assembly acting on the load plate to clamp the tissue between the load plate and the support means; and guide means operatively connected to the load plate and the flexure member for aligning the load plate relative to the support means and flexure member as the press assembly clamps the tissue between the load plate and the support means.

15. The apparatus as in claim 14 wherein said guide means comprises guide posts connected to said load plate that are slidably guided relative to the flexure member.

16. The apparatus as in claim 14 wherein said sensing means is a strain gage.

17. The apparatus as in claim 14 wherein the press assembly is joined to the flexure member and the load plate.

18. The apparatus as in claim 17 wherein the press assembly comprises an adjustment mechanism joined to the flexure member, the adjustment mechanism adjusting the relative spacing between the load plate and the flexure member.

19. The apparatus as in claim 18 wherein said adjustment mechanism comprises a threaded rod mating with a threaded aperture in the flexure member.

20. The apparatus as in claim 19 and further comprising a beam joined to said flexure member, said beam having said threaded aperture.

21. The apparatus as in claim 20 wherein said beam is joined to the connector wall.

22. A method to measure forces in a portion of tissue including the steps of:

providing a sensor assembly having a support plate, a substantially rigid load plate opposite said support plate, a flexure member joined to said load plate, the flexure member having a flexure sensing device;

locating said support plate to support a portion of tissue;

compressing the tissue between said load plate and said support plate;

generating a force in said tissue;

sensing the force transferred from said load plate to said flexure member; and providing an output signal from the flexure sensing device representative of the force.

23. The apparatus as in claim 22 wherein the sensor assembly includes adjusting means connected to said load plate, and wherein the step of compressing comprises adjusting said adjusting means to apply a selected compression force to said tissue.

24. The method as in claim 23 wherein the sensor assembly includes a frame joined to said support plate, and wherein said flexure member is cantilevered from said frame and comprises spaced parallel flexure plates and a connector wall, the flexure plates having first ends thereof attached to the frame, and second ends thereof joined with the connector wall.

25. The method as in claim 22 wherein said support plate is detachable from said sensor assembly, and wherein the method includes, after the step of providing the output signal, detaching the sensor assembly from said support plate with said support plate remaining in contact with said tissue.

26. The method as in claim 25 and after the step of detaching the sensor assembly, including the steps:

attaching said support plate to said sensor assembly;

recompressing the tissue between said load plate and said support plate;

generating a second force in said tissue;

sensing the second force transferred from said load plate to said flexure member; and providing a second output signal from the flexure sensing device representative of the second force.

27. The method as in claim 26 wherein the step of recompressing comprises adjusting said adjusting means to reapply substantially the selected compression force to said tissue.

* * * * *

UNITED STATES PATENT AND TRADEMARK OFFICE
CERTIFICATE OF CORRECTION

PATENT NO. : 5,289,826
DATED : March 1, 1994
INVENTOR(S) : Nebojsa Kovacevic

It is certified that error appears in the above-indentified patent and that said Letters Patent is hereby corrected as shown below:

Column 7, line 8, cancel "said" and insert --the--.

Column 8, line 15, cancel "apparatus" and insert --method--.

Signed and Sealed this

Nineteenth Day of July, 1994

Attest:

BRUCE LEHMAN

*Attesting Officer*     Commissioner of Patents and Trademarks